(12) United States Patent
Murata (10) Patent No.: US 7,973,144 B2
(45) Date of Patent: Jul. 5, 2011

(54) METHOD FOR REFOLDING PROTEIN (75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 378 days.

(21) Appl. No.: 12/296,918

(22) PCT Filed: Feb. 13, 2008

(86) PCT No.: PCT/JP2008/052788
§ 371 (c)(1),
(2), (4) Date: Oct. 10, 2008

(87) PCT Pub. No.: WO2008/114562
PCT Pub. Date: Sep. 25, 2008

(65) Prior Publication Data
US 2009/0275731 A1    Nov. 5, 2009

(30) Foreign Application Priority Data

Feb. 21, 2007   (JP) .................................. 2007-040903

(51) Int. Cl.
*C07K 1/04* (2006.01)
*C07K 1/113* (2006.01)
(52) U.S. Cl. ..................... 530/427; 530/402; 530/415
(58) Field of Classification Search ............... None
See application file for complete search history.

(56) References Cited

U.S. PATENT DOCUMENTS

| 2006/0194279 A1 | 8/2006 | Mizukami et al. | |
| 2007/0148044 A1 | 6/2007 | Murata | 422/82.01 |
| 2007/0298480 A1 | 12/2007 | Murata | 435/176 |

FOREIGN PATENT DOCUMENTS

| EP | 1 645 563 | 12/2006 |
| JP | 05-139717 | 6/1993 |
| JP | 2005-29531 | 2/2005 |
| JP | 2005-350383 | 12/2005 |
| JP | 2007-204403 | 8/2007 |

OTHER PUBLICATIONS

Cannone et al. Tracking Unfolding and Refolding of Single GFPmut2 Molecules. Biophysical Journal. Sep. 2005, vol. 89, No. 3, pp. 2033-2045.*

Rozema, et al., "Artificial Chaperones: Protein Refolding via Sequential Use of Detergent and Cyclodextrin", J. Am. Chem. Soc., vol. 117, 1995, pp. 2373-2374.

Ye, et al., "Polyvalent Carbocyanine Molecular Beacons for Molecular Recognitions", J. Am. Chem. Soc., vol. 126, No. 25, 2004, pp. 7740-7741.

Chiku, et al., "A novel protein refolding method using a zeolite", Analytical Biochemistry, vol. 348, 2006, pp. 307-314.

(Continued)

*Primary Examiner* — Jeffrey E Russel
(74) *Attorney, Agent, or Firm* — Fitzpatrick, Cella, Harper & Scinto (57) ABSTRACT

It has been required to refold an inactive protein into an active protein with high efficacy. This problem can be solved by the method for producing a protein including a step of providing a porous body supporting an inactive protein in its mesopores, a step of applying a denaturant to the porous body supporting the inactive protein, and a step of changing the inactive protein to an active protein by removing the denaturant from the porous body.

10 Claims, 6 Drawing Sheets

OTHER PUBLICATIONS

Wang, et al., "Protein Refolding Assisted by Periodic Mesoporous Organosilicas", Langmuir, vol. 23, 2007, pp. 5735-5739.
PCT International Search Report and Written Opinion of the International Searching Authority, Mailing Date Sep. 10, 2008.
U.S. Appl. No. 12/279,334, filed Aug. 13, 2008.
Kresge, et al., "Ordered mesoporous molecular sieves synthesized by a liquid-crystal template mechanism", Nature, vol. 359, pp. 710-712, Oct. 22, 1992.
Akbar, "Characterization of Beta-Zeolites by X-Ray Diffraction, Scanning Electron Microscope, and Refractive Index Techniques", J. Chem. Soc. Pak., vol. 32, No. 5, 2010, pp. 592-598.

* cited by examiner

METHOD FOR REFOLDING PROTEIN

TECHNICAL FIELD

The present invention relates to a method for producing a protein, which will find applications in development of a protein formulation and a new drug, enhancement of biosensor functions, and the like.

BACKGROUND ART

Owing to recent development of genetic engineering and protein engineering, methods for obtaining proteins have been changing, and among others a method, in which a gene encoding a target protein is isolated and expressed in an appropriate host cell, has enabled acquisition of a large amount of the target protein. For such synthesis of a protein from a gene, overexpression of the gene in *E. coli*, an insect cell or an animal cell, or a cell-free protein synthesis method is applied.

In case of protein synthesis using an insect cell or a mammal cell, the obtained protein often has a regulated higher order structure to form an ordered 3D-structure, and is soluble. By such methods, however, the yield of the target protein is very low, complex purification procedures are required to recover such protein, and long time is necessary to obtain the target protein. Further, the obtained target protein is very limited in a quantity, and is expensive.

On the other hand, protein synthesis using *E. coli* is easy in handling, requires only short time to obtain the target protein, and is inexpensive. Consequently, a method using an *E. Coli* transfected with a gene coding for synthesis of the target protein is the mainstream of the protein synthesis nowadays and a production process is being established. However, many observations have been reported concerning proteins of higher organisms including a human, which are produced by an *E. coli* expression system, that an aggregate of insolubilized protein called as an inclusion body is generated intracellularly. Such insolubilized protein of an inclusion body, of course, is lacking its inherent function or ability, and does not show activity. Consequently, in an artificial protein production process, it is required to unravel an inclusion body, to reform the higher structure, and to convert the protein to an active form with an ordered 3D-structure. Namely a refolding procedure of an inclusion body is necessary.

Such refolding is an important technology, which can be applicable not only to a protein produced by *E. coli* but also to reactivation of a protein deactivated by thermal history or other causes, and has been studied broadly. Various methods have been proposed, but they have attained only low levels of refolding rates, or better results only accidentally for some limited proteins.

For example, a method, by which an insolubilized protein is solubilized using a protein modifier such as urea or guanidine hydrochloride, and then refolded gradually by removing the protein modifier, is widely used. The method is, however, not satisfactory, since it requires time-consuming selection of the conditions for spontaneous refolding of a protein, and there remain many proteins which can be refolded by the method. The method cannot meet the current requirements for large quantity productions of proteins.

Under such circumstances, a refolding method using a molecular chaperone has received increased attention. A molecular chaperone, formerly known as a heat-shock protein, is a group of proteins which are known as proteins with functions concerning refolding, membrane permeability, association, decomposition of a protein, their gene sequences are highly conserved from *E. coli* to a human. Many of molecular chaperones are generated when an organism is subjected to a heat shock, metabolic inhibition, heavy metal, viral infection, ischemia, etc., and function to protect the organism against such stress and shock to maintain its homeostasis. However, their refolding mechanism has not been yet clarified. As an artificial molecular, chaperone β-cyclodextrin or cycloamylase is used. It is described in J. Am. Chem. Soc., Vol. 117, (1995) 2373-2374, that when a denatured protein is mixed with a solution of such artificial chaperone, inclusion and removal by the artificial chaperone take place and during such process the protein is refolded. The method has been successful only for such limited proteins as carbonicanhydrase B, and it is expensive since it is not recyclable.

Japanese Patent Application Laid-Open No. 2005-029531 has disclosed a method using zeolite beta. By the method, an inclusion body is contacted with zeolite beta and adsorbed on it, and then the inclusion body is desorbed by a surfactant to refold the protein which molecular weight can be higher than 100,000. Successful refolding has been confirmed with not less than several proteins. However, a selection of a surfactant for a desorption process from an adsorbent, zeolite beta, has a crucial impact on a refolding rate, and complex condition setting is required to address a specific nature of a protein. The process becomes more complex than other conventional refolding processes.

[Patent Document 1] Japanese Patent Application Laid-Open No. 2005-029531

[Non-patent Document 1] J. Am. Chem. Soc., Vol. 117, (1995) 2373-2374

DISCLOSURE OF THE INVENTION

Although various refolding methods have been reported, these methods have problems as described above. The present invention has been achieved considering such background art and an object of the present invention is to provide a method for producing a protein that enables easier and higher efficacy refolding.

The present invention provides a method for producing a protein, including the steps of:

providing a porous body supporting an inactive protein in the pores;

modifying the 3D-structure of the inactive protein by applying a denaturant to the porous body supporting the inactive protein; and changing the inactive protein to an active protein by removing the denaturant from the porous body.

The present invention provides a production method of a protein attaining a high refolding rate by refolding a protein within pores.

Further feature of the present invention will become apparent from the following description of exemplary embodiments with reference to the attached drawings.

BEST MODES FOR CARRYING OUT THE INVENTION

The outline of the present invention will be described referring to FIG. 1.

Figure 1A:
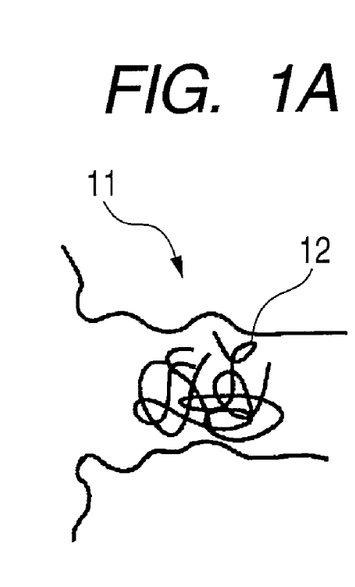
FIGS. 1A, 1B and 1C are schematic diagrams of an exemplary embodiment of the method for producing a protein according to the present invention.

As illustrated in FIG. 1(A), the method for producing a protein according to the present invention includes a step of providing a porous body 11 supporting within its pores an inactive protein 12. As illustrated in FIG. 1(B), follows a step of applying a denaturant 13 to the porous body 11 supporting the inactive protein 12, which cleaves a part of the bonds in the inactive protein 12 to change its 3D-structure. As illustrated in FIG. 1(C), further follows a step of changing the inactive protein 12 to an active protein 14 by removing the denaturant 13 from the porous body 11, in which step new bonds are formed for changing into an active protein 14.

The constituents of the present invention will be described in more detail.

(Protein)

Terms of "active protein" and "inactive protein" are used herein for proteins. "Active protein" herein refers to such protein, which retains its inherent substrate specificity. An example is a lysozyme protein which hydrolyzes specifically a β-1,4 linkage between N-acetylmuramic acid (MurNAc) and N-acetylglucosamin (GlcNAc), which exist in mucopeptide of bacterial cell wall. Other examples are a papain protein which decomposes specifically an immunoglobulin into Fab and Fc fragments, and an alcohol dehydrogenase protein which oxidizes alcohol to aldehyde.

On the other hand, "inactive protein" refers to such protein which does not retain its inherent substrate specificity. Concerning the aforementioned examples, if a lysozyme protein to the mucopeptide compound, a papain protein to an immunoglobulin, and a alcohol dehydrogenase to an alcohol, do not show respective substrate specificities, such proteins are classified to this group. Further herein "inactive protein" includes an inclusion body or an insolubilized protein generally produced in an *E. coli* expression system, which protein has a disordered 3D-structure. A protein inactivated by a thermal history or the like is also classified thereto.

(Mesopore and Porous Body)

Figure 2:
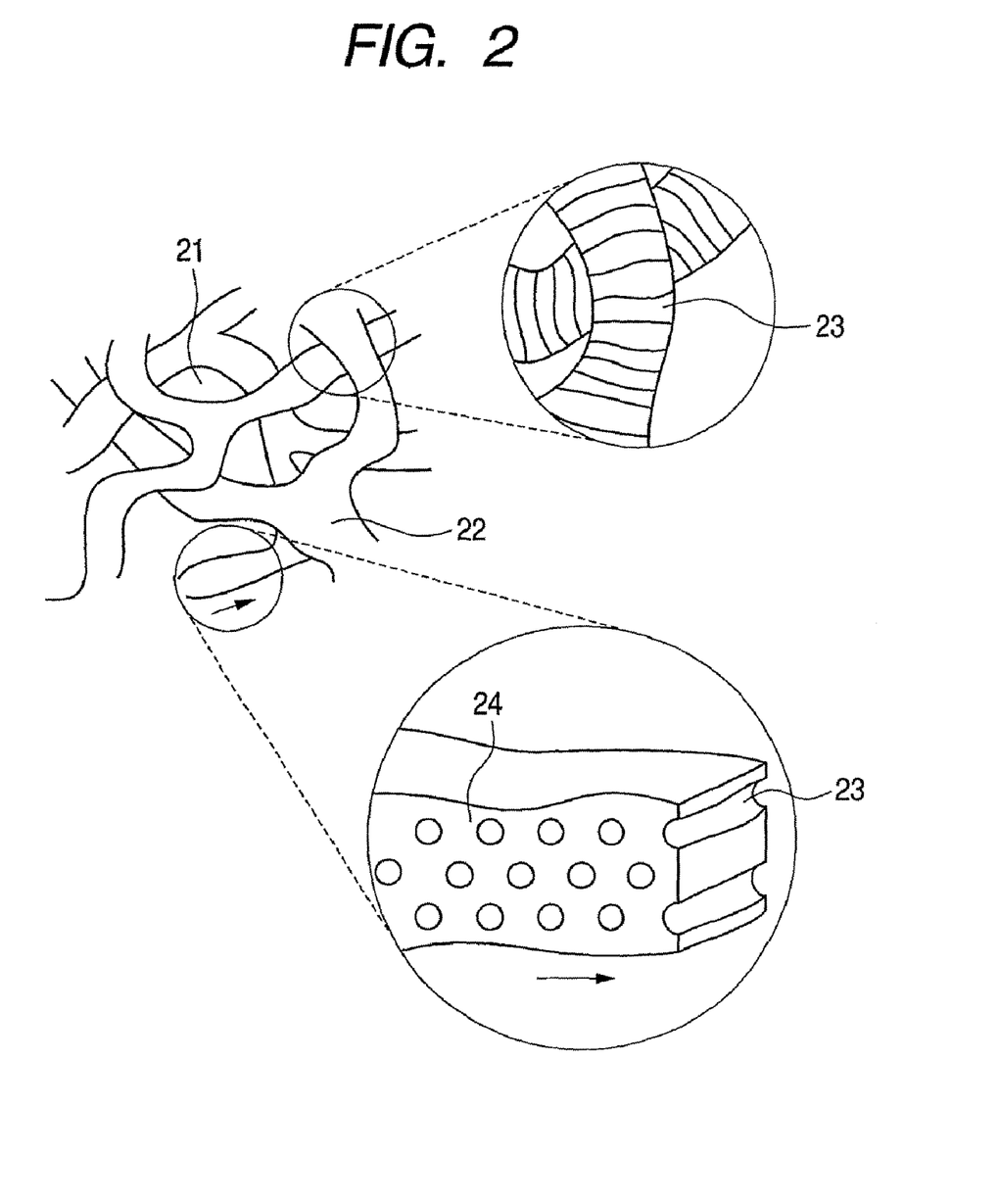
FIG. 2 is a schematic diagram for describing a minor-axis-oriented mesoporous material utilized in the Example.

Micropores in a "porous body" according to the present invention contain a "mesopore". As defined by IUPAC, a "mesopore" is a micropore having a pore diameter ranging from 2 nm to 50 nm. A preferable form of a "porous body" has, as illustrated in FIG. 2, a dendritic structure 22, in which a macropore 21 exists and mesopores 23 are oriented to a minor axis direction. Such porous body shows good diffusion of a protein, supports a large amount and allows high throughput in refolding. However, "porous body" in any other forms, such as spherical or membranous form, can be used, so long as similar efficacy is obtained. A "porous body" may be herein called as a porous material. A "porous body" with mesopores may be called as a mesoporous body or a mesoporous material.

The micropore structure of a porous body is illustrated in FIG. 2, which has mesopores of substantially uniform diameters. A 2D-hexagonal structure is illustrated in FIG. 2, although the arrangement of the micropores is not limited thereto. For example, cubic structure or 3D-hexagonal structure is also usable, so long as similar efficacy is obtained. Further, micropores with substantially uniform diameters, which arrangement is random, can also be suitable for producing a protein according to the present invention.

The mesopores of the porous body are built by surfactant micelles. The number of associated molecules building micelles is identical under certain conditions, and the identically figured micropores are constructed. While various forms, such as spherical, tubular and membranous forms, are known for micelles, a suitable micelle form building a mesoporous material according to the present invention is basically tubular. The tubules may be interconnected or separate.

With respect to mesoporous materials to be used according to the present invention, materials constituting the pore wall 24 of the porous body may be chosen from any materials which have the above-mentioned micropore structures. Examples are titanium oxide, tin oxide and silicon oxide. Among others, a material having a component of silicon can be used, and especially silica is preferable. Further an organic silica hybrid material including an organic group having 1 or more carbon atoms, 2 or more silicon atoms bonded with the organic group at 2 or more sites, and 1 or more oxygen atoms bonded with the silicon atoms, can be used.

Among mesoporous materials prepared using a template of surfactant micelles, mesoporous materials with a small aspect ratio of a pore length and a pore diameter is suitable for the present invention. The method is disclosed by the following document: Journal of the American Chemical Society Vol. 126, p. 7740.

However, a mesoporous material usable according to the present invention is not limited to the product of the exemplified documented method, and any other materials meeting the aforementioned characteristics of mesoporous materials can be used.

(A Method for Producing a Porous Body)

A method for synthesizing minor-axis-oriented mesoporous silica based on a sol-gel process, used according to the present invention will be described below.

A reaction solution contains as raw materials a surfactant, an organic compound, and a metal alkoxide. Depending on a material of the micropore wall, an appropriate amount of a hydrolysis catalyst such as an acid may be added.

Depending on an end material, a raw material is chosen from a halide, a chalcogen compound, a metal alkoxide, etc. For example, if a micropore wall is silica, a metal alkoxide such as tetraethoxysilane or tetramethoxysilane can be preferably used. Naturally, silica sources other than an alkoxide are applicable to the present invention.

As a surfactant, a nonionic surfactant such as a block-copolymer containing polyethylene oxide as a hydrophilic group is used. However, usable surfactants are not limited thereto, and any one forming the aimed structure can be used without particular limitation.

The micropore structure with a small aspect ratio is regulated by an added organic molecule and its addition amount. For example, addition of n-decane directs to synthesis of a rod-shaped mesoporous silica having a micropore structure with a small aspect ratio.

As an acid, a general acid, such as hydrochloric acid or nitric acid, can be used.

The aforementioned reaction solution is reacted under hydrothermal conditions to synthesize an aimed mesoporous material. The reaction temperature can be selected in a temperature range from 80° C. to 150° C. The reaction time can be selected between several hours and several days. They may be adjusted for optimization.

The synthesized mesoporous material is washed by pure water and left for air-drying to form an inorganic-organic complex powder material having surfactant micelles as a template in micropores. A mesoporous material, which is usable for the purpose of the present invention, can be prepared by removing the template surfactant micelles from the inorganic-organic complex powder material. There are many methods for removing a surfactant, and any method can be used so long as the microporous structure is not destroyed by the removal of a surfactant.

The most commonly used method is burning in an oxygen-containing atmosphere. For example, a synthesized material is burnt in air at 500° C. for 10 hours to remove completely a surfactant substantially without destroying the mesoporous structure. It is preferable to optimize the burning temperature and time according to a material building the microporous wall and a surfactant to be used.

(Inspection of a Porous Body)

A thus synthesized mesoporous powder sample is tested by a nitrogen gas adsorption-and-desorption measurement to determine micropore diameters. A mesoporous material according to the present invention is characterized by its substantially uniform micropore diameters. Micropores with uniform diameters mean hereunder that a single peak is observed in the micropore diameter distribution analyzed by Berret-Joyner-Halenda (BJH) method using the result of the nitrogen gas adsorption measurement, and that not less than 60% of the mesopores have diameters within the 10 nm-width range. The micropore diameter can be changed by a selection of a surfactant as described later.

It is possible to know a periodic structure of a micropore by an X-ray diffraction measurement (XRD). A mesoporous material according to the present invention is characterized in that a XRD result shows at least one diffraction peak in the angle range corresponding to a structural period not less than 1 nm.

(Refolding Using a Porous Body)

Next, a method for activating an inactive protein by a refolding process using the porous body will be described.

Figure 1B:
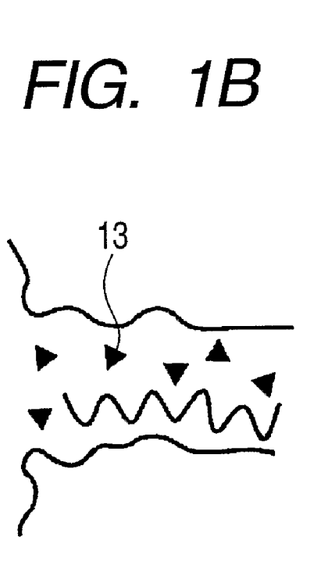
Figure 1C:
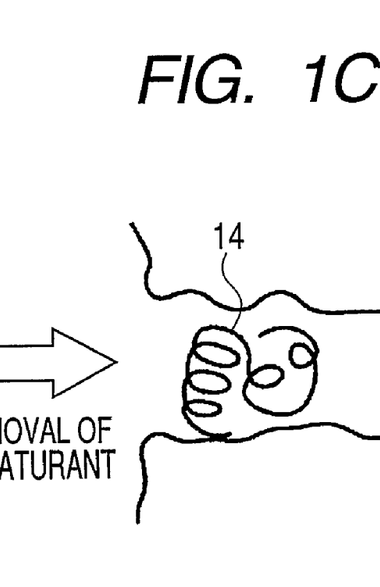

The refolding process using a mesoporous body with an inclusion body 12 of a deactivated protein and a denaturant 13 is illustrated schematically in FIGS. 1A to 1C.

According to the present invention, the target protein for refolding may be an inclusion body, or an inactive protein deactivated by a thermal history or other causes. According to the present invention, such protein is activated through refolding of its 3D-structure by a treatment of the protein in mesopores of mesoporous bodies.

In the step of activating a protein, an inclusion body of a protein is first dispersed/dissolved in a solution containing a denaturant, and adsorbed in micropores of mesoporous bodies mixed into the solution. The denaturant is then removed using a concentration gradient method, or the protein in the micropores of the mesoporous bodies is deactivated by a thermal history, then a denaturant is added, and the denaturant is removed during the step. Naturally it is possible to disperse porous bodies, which have already carried an inactive protein, into a solution containing a denaturant.

As a dispersing solvent for a protein prior to adsorption by mesoporous bodies, commonly, but not limited to, water is used, since the protein is generally produced by an expression system of *E. coli*, is used usually in a water solution, and exists often in water solution even in deactivated form.

According to the present invention unfolding of a protein is carried out using a denaturant to ease unfolding and refolding of entangled protein chains of an inclusion body, etc. Additionally, some reducing agent may be used to break a disulfide bond generated unwillingly in a protein chain. According to the present invention, no other refolding factors such as a surfactant, which are conventionally used, are added.

A denaturant is, in a broader sense, an agent, which modifies a 3D-structure of a protein. Herein it is divided into a denaturant and a reducing agent for explanation.

Urea and guanidine hydrochloride are examples of denaturants. It is considered that a denaturant according to the present invention should better be able to cleave a hydrogen bond and a hydrophobic bond in a protein. Mercaptoethanol, glutathione and dithiothreitol are examples of reducing agents. It is considered that a reducing agent according to the present invention should better be able to cleave a disulfide bond in a protein.

An unfolded protein can be refolded by removal of a denaturant. While there is no limitation on a removal method, including a dilution method or a dialysis method, which is able to remove a denaturant, a dilution method based on concentration gradient is preferable. Since unfolded proteins dispersed in micropores are resistant to coagulation by a steeper concentration gradient, the dilution time can be shortened to several hours.

Refolded proteins are trapped in micropores by physical adsorption, wherein contribution of electrostatic adsorption is dominant. Consequently, by changing pH of a buffer solution or by ion-exchanging, they can be desorbed out of the micropores. Thus, by supporting in such mesopores, the dilution time can be shortened and the 3D-structure of proteins can be restructured more accurately.

The present invention will now be described in more detail by way of an example thereof, provided that the example should not be interpreted in any restrictive way.

EXAMPLE 1

In this Example, a mesoporous silica is prepared, in which branched rod-shaped 3D-networked silica forms a porous material having macropores and substantially uniform tubular mesopores oriented parallel to a minor axis of the rod. An optional amount of lysozyme is adsorbed on it, deactivated by heat and refolded by adsorption/desorption of a denaturant. As a nonionic surfactant, 2.40 g of tri-block copolymer [$EO_{20}PO_{70}EO_{20}$; $HO(CH_2CH_2O)_{20}(CH_2CH(CH_3)O)_{70}(CH_2CH_2O)_{20}H$] was dissolved in 76.5 mL of pure water, 7.5 mL of 36 wt % concentrated hydrochloric acid was added, and the resultant mixture was stirred at room temperature for 30 min. After dissolution, the water solution was kept cooled in a thermostat bath at between 18° C. and 30° C. for 2 hours. After addition of 13.9 g of n-decane, it was left stirred for 1 day. 0.027 g of $NH_4F$ as a hydrolysis catalyst and 5.10 g of tetraethoxysilane (TEOS) were added in the mixture solution to form a precursor solution. The final composition (mol ratio) of the precursor solution was adjusted to TEOS:HCl:$EO_{20}PO_{70}EO_{20}$:$NH_4F$:n-decane:$H_2O$=0.25:0.9:0.004:0.007:1:42.9.

The precursor solution was stirred at the above-mentioned temperature for 1 day, and transferred into a pressure vessel for reaction at 100° C. for 24 hours. The resultant white precipitate was washed thoroughly with pure water and then vacuum dried.

The obtained powder sample was burnt in air at 500° C. to remove/decompose a surfactant in micropores. The removal of organic chemicals such as a surfactant was confirmed by IR spectroscopy.

Figure 3:
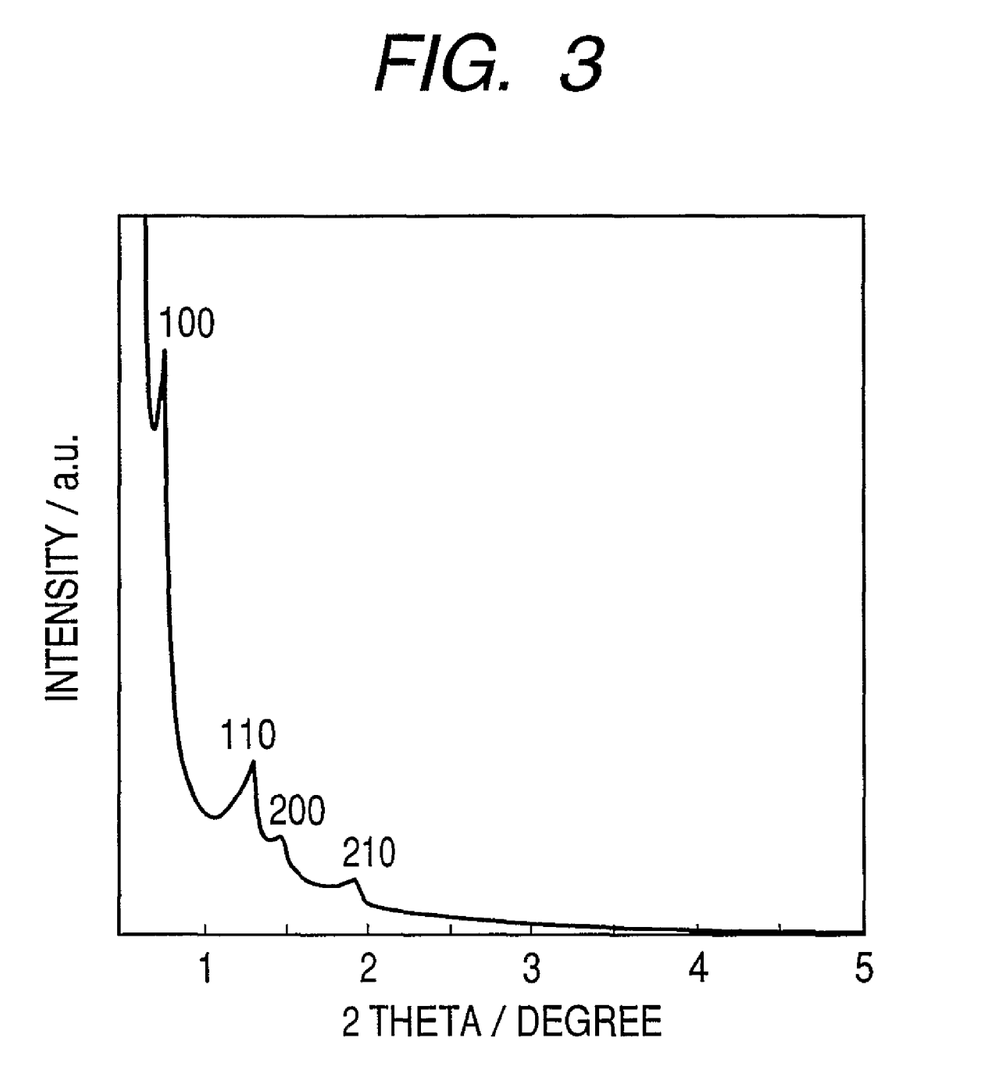
FIG. 3 is a chart of the X-ray diffraction result of a minor-axis-oriented mesoporous material utilized in the Example.

The synthesized mesoporous silica powder was analyzed by X-ray diffraction method, to detect diffraction peaks assigned to (100) plane of hexagonal structure with interplanar spacing of 11.7 nm, as well as diffraction peaks assigned to (110), (200), (210) planes as illustrated in FIG. 3. The results indicate that the micropore structure of the mesoporous silica has hexagonal configuration with high degree of regularity.

The result of a nitrogen adsorption/desorption isotherm analysis in 77 K showed Type IV of IUPAC Adsorption/Desorption Isotherm Classifications. The specific surface area according to B.E.T. method was calculated to give 700 $m^2/g$ and the pore volume was 1.88 mL/g. Further, calculation of micropore diameter by BJH method using the adsorption/desorption isotherm results showed that the mesoporous silica synthesized in this Example had a narrow micropore diameter distribution with a single peak of 14.1 nm, and more than 90% of the micropores were within the distribution width of 10 nm.

Figure 4:
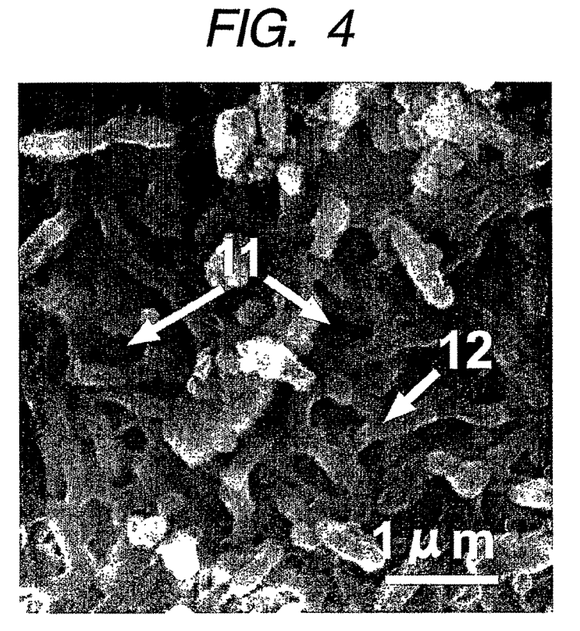
FIG. 4 is an image of the electron scanning microscopy of a minor-axis-oriented mesoporous material utilized in the Example.
Figure 5:
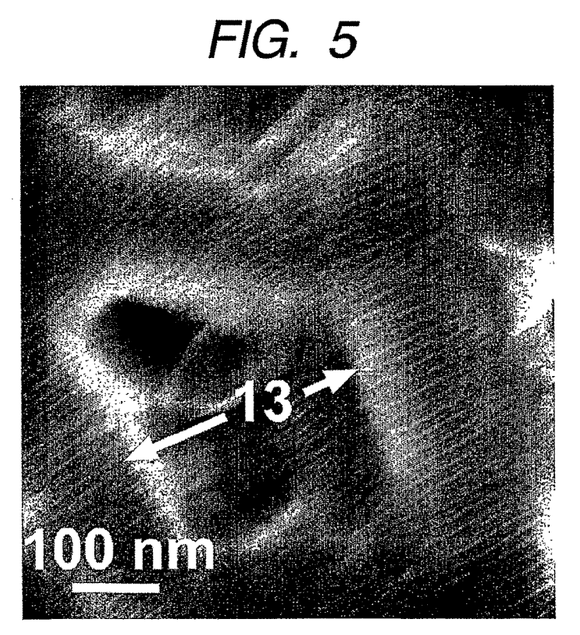
FIG. 5 is a high-magnification image of the electron scanning microscopy of a minor-axis-oriented mesoporous material utilized in the Example.
Figure 6:
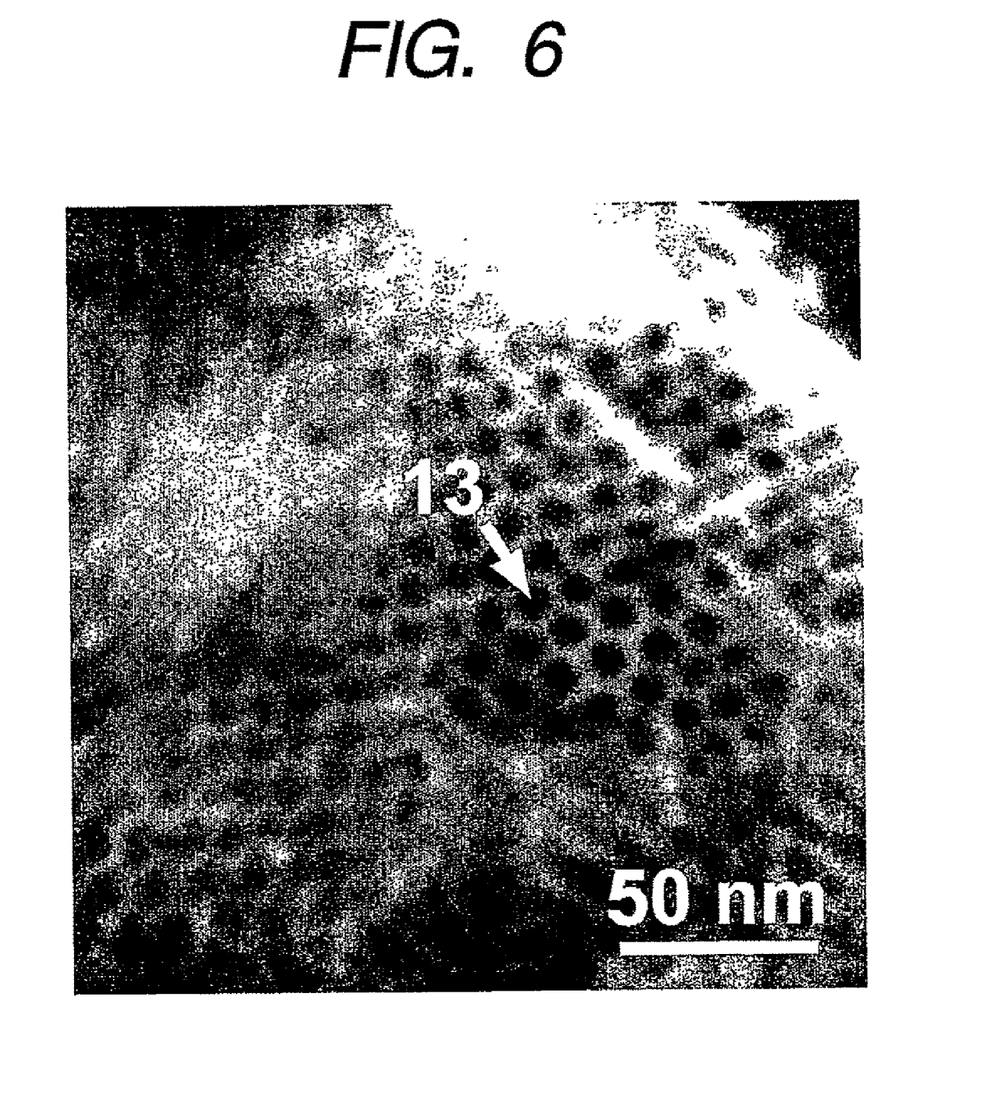
FIG. 6 is a high-magnification image of the electron scanning microscopy of a section of the minor-axis-oriented mesoporous material illustrated in FIG. 4.

According to observation with scanning electron microscopy (SEM), as shown in FIG. 4, the product formed numerously branched rod-shaped components and a 3D-networked structure of such components. The space among the branched rod-shaped components formed a macropore with a 300 to 500 nm diameter. The diameters of the rod-shaped components were 200 to 300 nm. According to observation with SEM at higher magnification as shown in FIG. 5, tubular mesopores with a diameter of 14 nm were oriented in the direction of the minor axes of the dendritic components. According to a section view as shown in FIG. 6, comparatively uniform tubular mesopores were packed to form a honeycomb micropore structure.

Then lysozyme as a model protein was adsorbed in mesopores of mesoporous silica. Lysozyme is known as an enzyme difficult to be refolded, since it has 4 disulfide bonds within its structure.

Using a 10 mM phosphate buffer solution (pH 7.4), lysozyme was prepared to 0.2 mg/mL. Into 1 mL of this solution was added 2.0 mg of the mesoporous silica synthesized according to the above-mentioned method. The mixture was stirred with a shaker at 4° C. for 24 hours to adsorb the lysozyme in the micropores of the mesoporous silica. After stirring, the mixture was centrifuged at 20,000 g at 4° C. for 10 min. to obtain silica with immobilized lysozyme. The adsorption amount of lysozyme on the mesoporous silica was determined using an absorbance maximum at 280 nm for the supernatants before and after the adsorption. Adsorption of about 100 mg/g was confirmed and an adsorption isotherm curve showed a Langmuir type monolayer adsorption. With a nitrogen adsorption measuring apparatus, a change of adsorption behaviors of nitrogen molecules in micropores between before and after the adsorption of lysozyme on the mesoporous silica was investigated to confirm that lysozyme was adsorbed not on the outer surface but in micropores of the mesoporous silica.

Then the mesoporous silica with immobilized lysozyme was heat-treated and a measurement of refolding was carried out.

The prepared mesoporous silica with immobilized lysozyme was washed, and, after addition of 1 mL of 10 mM phosphate buffer (pH 7.0), was heated at 90° C. for 2 hours. To the resultant mixture 2 mL of a mixture solution of 6 M guanidine hydrochloride solution and 20 mM β-mercaptoethanol was added and left stirred for 12 hours. Then refolding process was carried out by washing with pure water repeatedly at intervals of 1 to 6 hours. Refolding was evaluated by a measurement of the activity of lysozyme. In addition to the measurement of the final product in the refolding process, the activities of lysozyme immediately after immobilization, and after heat-treatment were measured as controls. The method for measuring activity of lysozyme will be described below.

Figure 7:
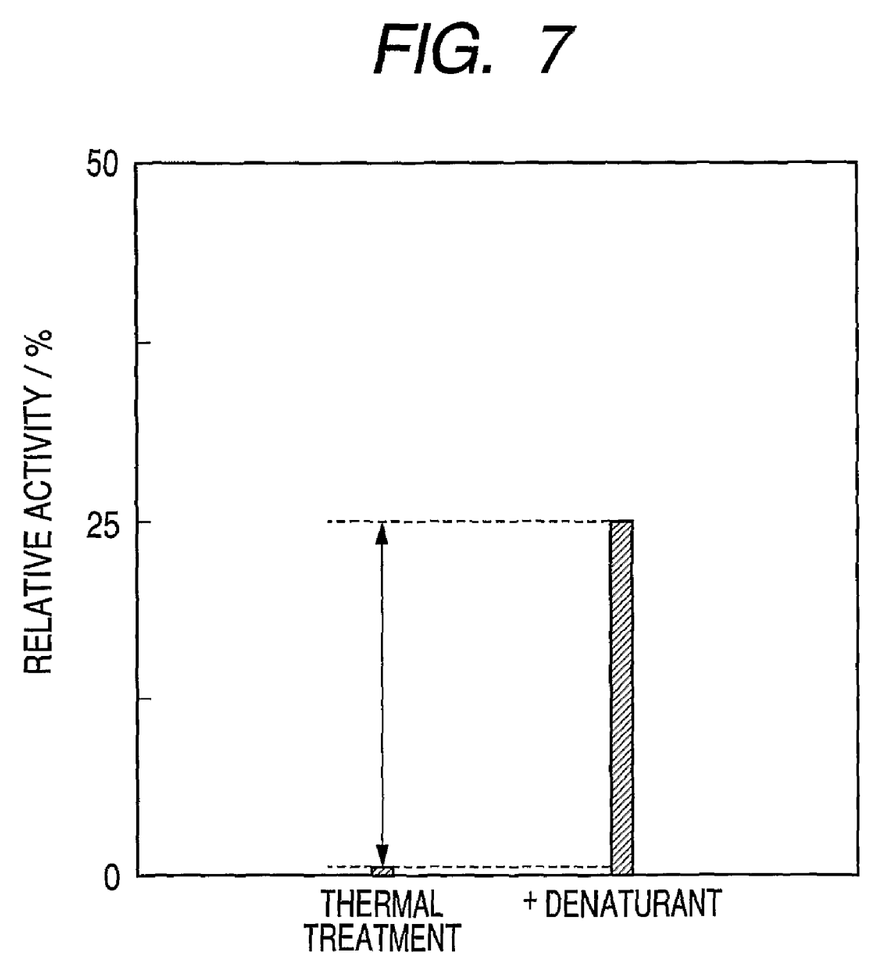
FIG. 7 shows a comparison of the activity of lysozyme after heat-treatment and the activity of lysozyme after completion of the production method of the Example.

A mesoporous silica with immobilized lysozyme was washed. Separately, 230 μL of a 1.5 mg/mL solution of p-nitrophenyl-penta-N-acetyl-β-chitopentaoside (PNP-GlucNAc) prepared with 50 mM sodium acetate buffer (pH 5.0) was provided. Also 100 μL of a 0.012 mg/mL solution of N-acetylglucosaminidase from Jack beans (NAHase) prepared with 10 mM phosphate buffer (pH 7.0) was provided. They were mixed in 50 mM sodium acetate buffer (pH 5.0) and the mixture was stirred at 37° C. for 1 hour. Since p-nitrophenol was formed in the presence of activated lysozyme, the absorbance peak was measured at 405 nm to evaluate the lysozyme activity. FIG. 7 illustrates relative activities with respect to the activity of lysozyme before heat-treatment defined as 100%. The activity of lysozyme after the heat-treatment was almost 0%. Only by the step of addition and the removal of the denaturant, not less than 20% of lysozyme was refolded.

Further, the activity of lysozyme desorbed from the mesoporous body was measured. To the sample containing lysozyme refolded by removal of the denaturant, 50 mM to 100 mM phosphate buffer solution was added and stirred for 12 hours to desorb the lysozyme out of micropores. After the completion of stirring, the mixture was centrifuged at 20,000 g at 4° C., for 10 min. to precipitate mesoporous silica and the supernatant containing lysozyme was collected for measurement of the lysozyme activity according to the above method. The lysozyme activity decreased to about 10%, although activated lysozyme was confirmed to be desorbed from the mesoporous body.

COMPARATIVE EXAMPLE 1

In this Comparative Example, the refolding effect of the refolding process described in Example 1 was measured for the cases with monodispersed spherical silica without homogeneous micropores, and with cubic mesoporous silica of pore diameter 2.9 nm. A method for synthesizing the monodispersed spherical silica is disclosed in Japanese Patent Application Laid-Open No. H05-139717, and a method for synthesizing the cubic mesoporous silica, in Nature, Vol. 359, p. 710.

The synthesized monodispersed spherical silica had an average diameter of about 50 nm according to SEM observation, and the cubic mesoporous silica had a specific surface area of 900 $m^2/g$ and a micropore diameter of 2.9 nm according to nitrogen absorption isotherm measurement.

Refolding tests of lysozyme similar to those in Example 1 were carried out using the two samples. Using 10 mM phosphate buffer solution (pH 7.4), lysozyme was prepared to 0.2 mg/mL. Into 1 mL each of this solution was added respectively 2.0 mg of the mesoporous silica synthesized according to the above-mentioned methods. The mixture was stirred with a shaker at 4° C. for 24 hours to adsorb the lysozyme on the mesoporous silica. After the completion of stirring, the mixture was centrifuged at 20,000 g at 4° C., for 10 min. to obtain silica with immobilized lysozyme. The adsorption amounts of lysozyme on mesoporous silica were determined using an absorbance maximum at 280 nm for the supernatants before and after the adsorption. Adsorption of about 10 mg/g was confirmed, respectively. With a nitrogen adsorption measuring apparatus, a change of adsorption behaviors of nitrogen molecules between before and after the adsorption of lysozyme on the mesoporous silica was investigated to confirm that lysozyme was not introduced into the micropores, but adsorbed on the outer surface. It was presumed that the pores were not big enough to accommodate lysozyme with a size of about 3 nm.

After heat-treatment of mesoporous the silica with immobilized lysozyme, the refolding efficacy was tested. The prepared mesoporous silica with immobilized lysozyme was washed, and, after addition of 1 mL of 10 mM phosphate buffer (pH 7.0), was heated at 90° C. for 2 hours. To the resultant mixture, 2 mL of a mixture solution of 6 M guanidine hydrochloride solution and 20 mM β-mercaptoethanol was added and the mixture was left stirring for 12 hours. Then refolding process was carried out by washing with pure water repeatedly at intervals of 1 to 6 hours. Refolding was evaluated by a measurement of activity of lysozyme. In addition to the measurement of the final product in the refolding process, the activities of lysozyme immediately after immobilization and after heat-treatment were measured as controls. The method for measuring activity of lysozume will be described below.

The mesoporous silica with immobilized lysozyme was washed. Separately, 230 µL of a 1.5 mg/mL solution of p-nitrophenyl-penta-N-acetyl-β-chitopentaoside (PNP-GlucNAc) prepared with 50 mM sodium acetate buffer (pH 5.0) was provided. Also, 100 µL of a 0.012 mg/mL solution of N-acetylglucosaminidase from Jack beans (NAHase) prepared with 10 mM phosphate buffer (pH 7.0) was provided. They were mixed in 50 mM sodium acetate buffer (pH 5.0) and the mixture was stirred at 37° C. for 1 hour. Since p-nitrophenol was to be formed in the presence of activated lysozyme, the absorbance was measured at 405 nm to evaluate the lysozyme activity. Both the samples in this Comparative Example did not show absorbance at 405 nm, indicating that they did not have activity like the heat-treated sample and that the step of addition and the removal of the denaturant alone did not cause refolding for adsorption outside micropores.

As demonstrated by comparison of the Comparative Example simulating a conventional refolding technology which has been already disclosed with the Example of the present invention, it is shown that the present invention provides refolding technology having higher efficiency.

INDUSTRIAL APPLICABILITY

The present invention will find industrial applications in a protein formulation, a new drug, a biosensor with active functions, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-040903, filed Feb. 21, 2007, which is hereby incorporated by reference herein in its entirety.

The invention claimed is:

1. A method for refolding a protein, comprising the steps of:
   providing a mesoporous silica which has a pore diameter ranging from 2 nm to 50 nm and which supports an inactive protein in the pores;
   modifying the 3D-structure of the inactive protein by applying a denaturant to the mesoporous silica supporting the inactive protein; and
   changing the inactive protein to an active protein by removing the denaturant from the mesoporous silica.

2. The method for refolding a protein according to claim 1, wherein the denaturant cleaves a hydrogen bond or a hydrophobic bond in the inactive protein.

3. The method for refolding a protein according to claim 1, wherein the step of changing to the active protein is a step of forming a new hydrogen bond or a new hydrophobic bond in the protein supported in the mesoporous silica.

4. The method for refolding a protein according to claim 1, wherein the inactive protein is a protein deactivated by a thermal history.

5. The method for refolding a protein according to claim 1, comprising a step of recovering the active protein out of the mesoporous silica.

6. The method for refolding a protein according to claim 1, wherein mesopores of the mesoporous silica are arranged in a honeycomb form.

7. The method for refolding a protein according to claim 1, wherein a reducing agent is additionally applied in the step of applying the denaturant.

8. The method for refolding a protein according to claim 1, wherein by an X-ray diffraction analysis of the mesoporous silica, the diffraction chart shows at least one diffraction peak in an angle range corresponding to a structural period not less than 1 nm.

9. The method for refolding a protein according to claim 1, wherein the mesoporous silica contains dendritic components, and the pores are tubular mesopores and oriented in the direction of the minor axes of the dendritic components.

10. The method for refolding a protein according to claim 9, wherein the mesopores are packed to form a honeycomb micropore structure.

* * * * *